(12) United States Patent
Kothari et al.

(10) Patent No.: US 11,376,444 B1
(45) Date of Patent: Jul. 5, 2022

(54) INTRAORAL PHOTOTHERAPY DEVICE

(71) Applicant: Mureva Phototherapy Inc., Strongsville, OH (US)

(72) Inventors: Vedang Kothari, Cleveland, OH (US); Jordan W. Oja, Stow, OH (US); Jason D. Lazzara, Cleveland, OH (US); Samuel J. Shelnutt, Olmsted Township, OH (US)

(73) Assignee: MUREVA PHOTOTHERAPY INC., Strongsville, OH (US)

( * ) Notice: Subject to any disclaimer, the term of this patent is extended or adjusted under 35 U.S.C. 154(b) by 0 days.

(21) Appl. No.: 17/150,304

(22) Filed: Jan. 15, 2021

(51) Int. Cl.
*A61N 5/06* (2006.01)

(52) U.S. Cl.
CPC .... *A61N 5/0603* (2013.01); *A61N 2005/0606* (2013.01); *A61N 2005/0626* (2013.01); *A61N 2005/0632* (2013.01); *A61N 2005/0645* (2013.01); *A61N 2005/0668* (2013.01)

(58) Field of Classification Search
CPC .......... A61N 5/0603; A61N 2005/0606; A61N 2005/0626; A61N 2005/0632; A61N 2005/0645; A61N 2005/0668
See application file for complete search history.

(56) References Cited

U.S. PATENT DOCUMENTS

| | | | |
|---|---|---|---|
| 2004/0191729 A1* | 9/2004 | Altshuler | A61F 7/00 433/215 |
| 2007/0259310 A1* | 11/2007 | Goodson | A61C 19/066 433/29 |

* cited by examiner

*Primary Examiner* — Lindsey G Wehrheim

(57) ABSTRACT

An intraoral phototherapy device is provided that improves tissue illumination. Oral tissue illumination is particularly difficult inside of the teeth. That is, it is particularly difficult to illuminate the roof of the mouth, floor of the mouth, sides of the tongue, and/or ventral surface of the tongue. The intraoral phototherapy device improves illumination of these tissues using a bifurcated central projection that receives a portion of the tongue. An intraoral phototherapy device is also provided that includes a breathing tube to improve patient breathing and vocalization for enabling illumination of tissues at the back of the mouth. An intraoral phototherapy device is additionally provided that allows for separate control of light emission from different areas of the intraoral phototherapy device.

29 Claims, 11 Drawing Sheets

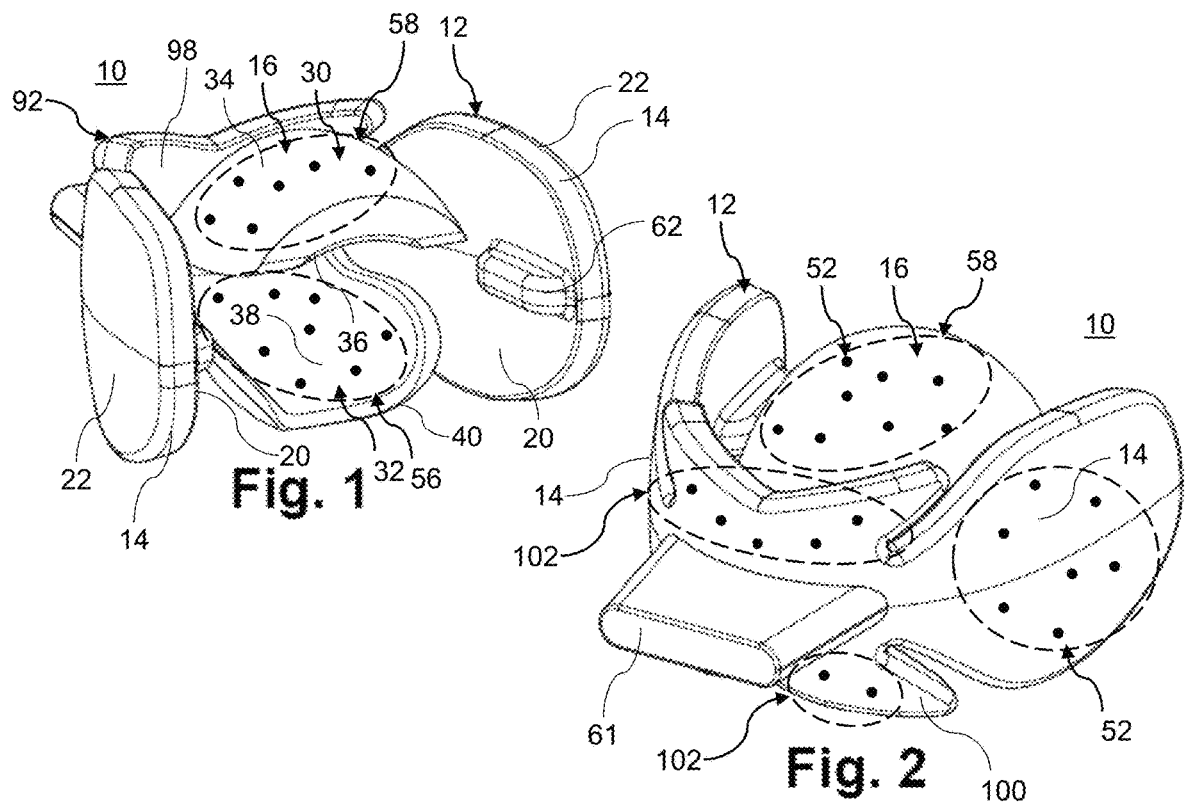
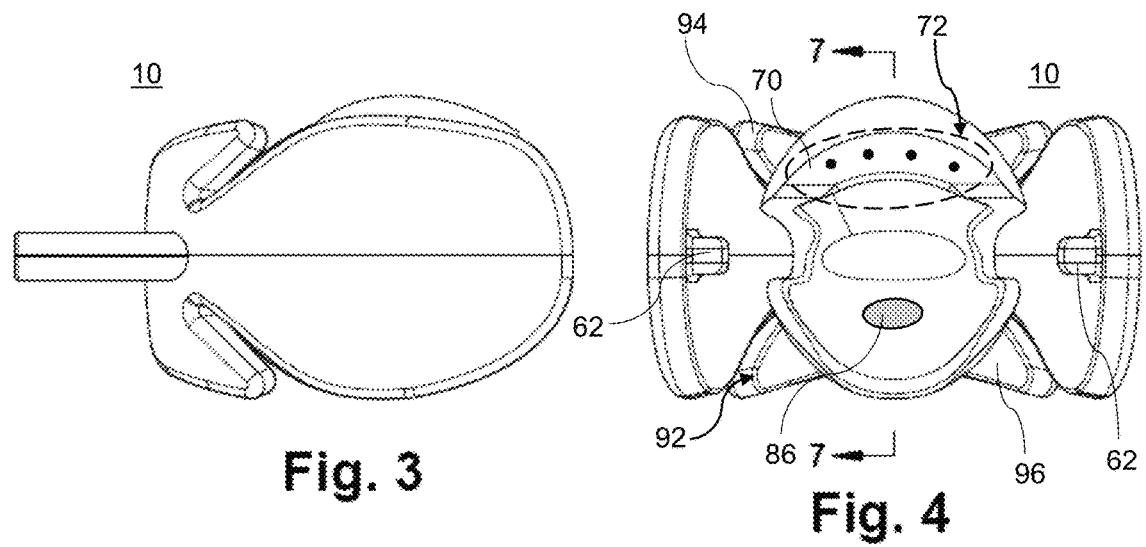

US 11,376,444 B1

INTRAORAL PHOTOTHERAPY DEVICE

TECHNICAL FIELD

This present disclosure relates generally to phototherapy and more particular to intraoral phototherapy devices.

BACKGROUND

Phototherapy can be utilized for treating and providing pain relief for various conditions, including a condition called Oral Mucositis (OM). Phototherapy can be delivered in several ways, e.g., directly to the tissue via Low Level Laser Therapy (LLLT) or via a light emitting diode (LED) array that propagates light through the skin into the affected region.

Currently there are two known methods for administering phototherapy for the treatment of various phototherapy treatment conditions of the mouth including, but not limited to Oral Mucositis (OM), low level laser therapy and light emitting diode (LED) arrays. Oral Mucositis is one of the most common and highly significant toxicities of cancer therapy.

Barriers to the acceptance of low-level laser therapy include the cost of laser equipment and the labor intensiveness. Additionally, there are problems with interoperator variability and the need for specialized training. Also patients receiving this form of treatment are required to hold their mouths open for long periods of time which is uncomfortable and becomes extremely painful as the Mucositis progresses.

LED arrays utilize a plurality of LEDs to irradiate larger areas of tissue externally. The light from these arrays penetrates the skin to stimulate the mucosal membrane. LED arrays have the advantage of irradiating a large surface area, are simpler to implement than spot laser systems, and are more comfortable to the patient. The main disadvantages of using LED arrays for administering phototherapy treatment is that they lack dose control because they must transilluminate cheek tissue and have difficulty reaching all regions of the oral cavity, including the tonsillar and palatal regions which are highly susceptible to OM. Also variability in tissue thickness between different buccal regions and different patients makes it impossible to accurately monitor and control the dose of light administered to the mucosa.

SUMMARY

The present disclosure provides an intraoral phototherapy device including a bifurcated central projection for illuminating a roof of the oral cavity, a floor of the oral cavity, and one or more surfaces of the tongue.

The present disclosure also provides an intraoral phototherapy device having a breathing tube to improve patient breathing and to allow patient vocalization to improve illumination of tissues at the back of the mouth.

The present disclosure further provides an intraoral phototherapy device allowing separate control of light emission from different areas of the intraoral phototherapy device, such that different tissues receive different optical doses.

While several features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages, and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

FIG. 1 is a front perspective view of an embodiment of an intraoral phototherapy device.

FIG. 2 is a rear perspective view of the intraoral phototherapy device of FIG. 1.

FIG. 3 is a side view of the intraoral phototherapy device of FIG. 1.

FIG. 4 is a front view of the intraoral phototherapy device of FIG. 1.

Figure 5:
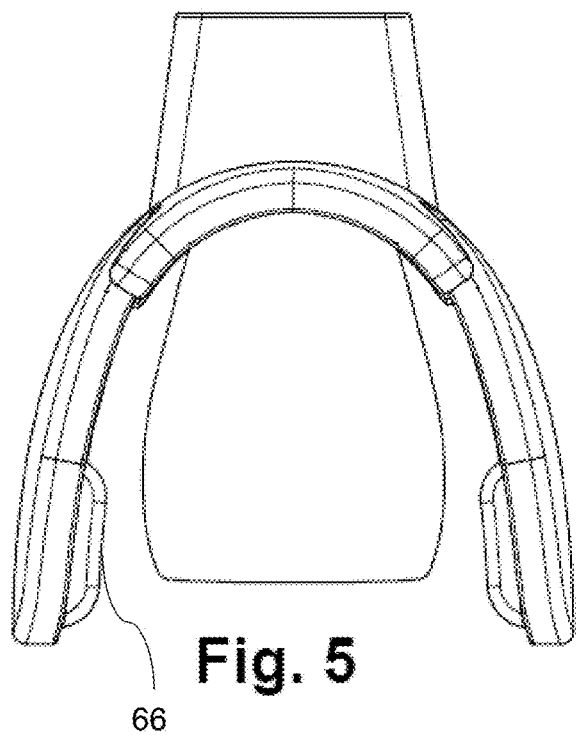
FIG. 5 is a top view of the intraoral phototherapy device of FIG. 1.
Figure 6:
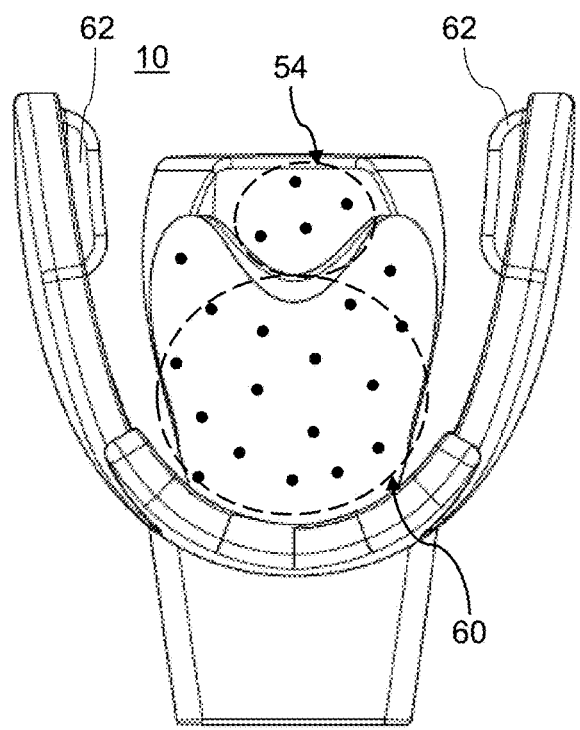
FIG. 6 is a bottom view of the intraoral phototherapy device of FIG. 1.
Figure 7:
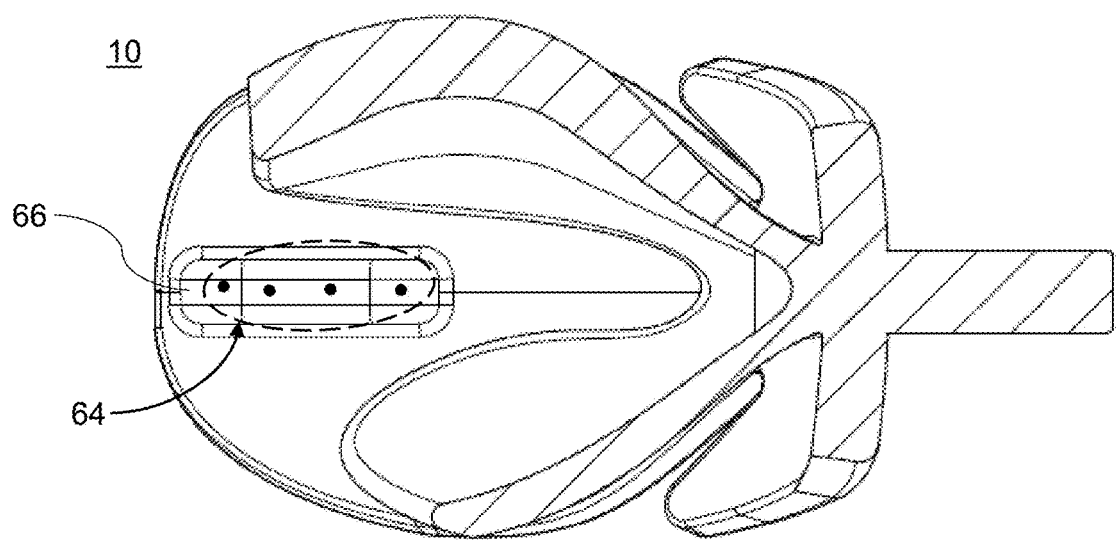
FIG. 7 is a side cut away view of the intraoral phototherapy device of FIG. 4.
Figure 8:
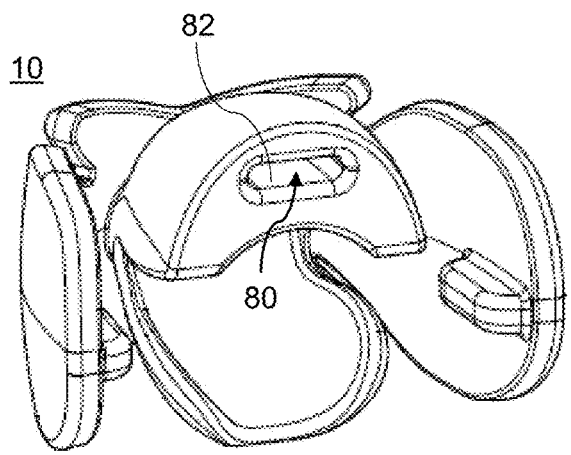
FIG. 8 is a top front perspective view of another embodiment of the intraoral phototherapy device.
Figure 9:
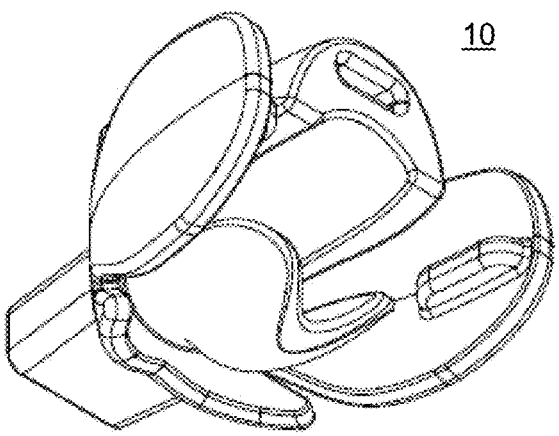
FIG. 9 is a lower front perspective view of the intraoral phototherapy device of FIG. 8.
Figure 10:
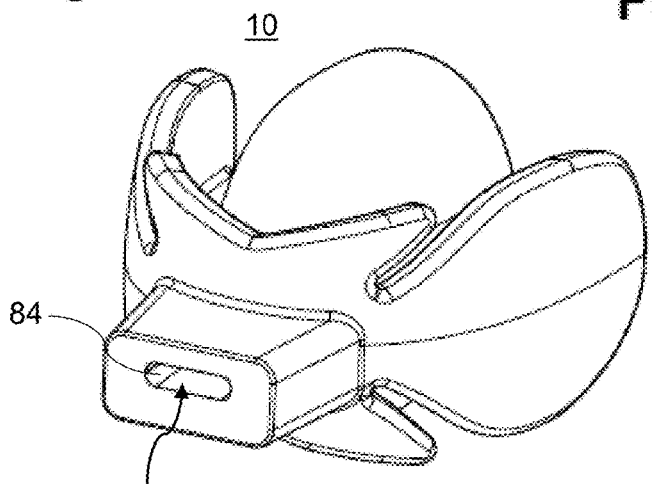
FIG. 10 is a rear perspective view of the intraoral phototherapy device of FIG. 8.
Figure 11:
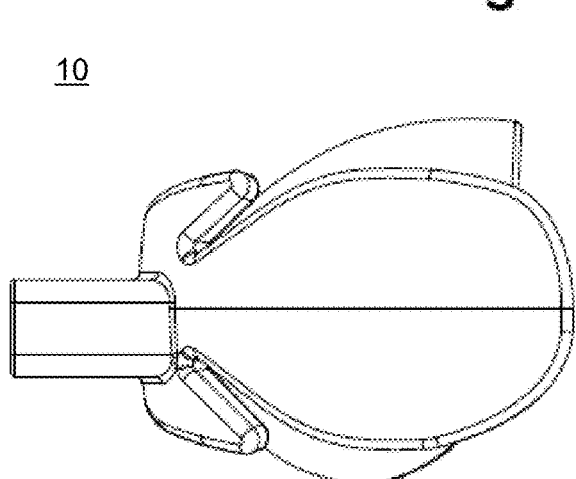
FIG. 11 is a side view of the intraoral phototherapy device of FIG. 8.
Figure 12:
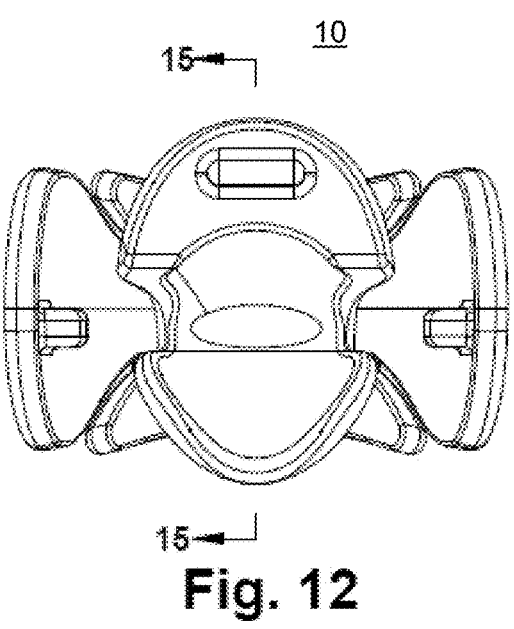
FIG. 12 is a front view of the intraoral phototherapy device of FIG. 8.
Figure 13:
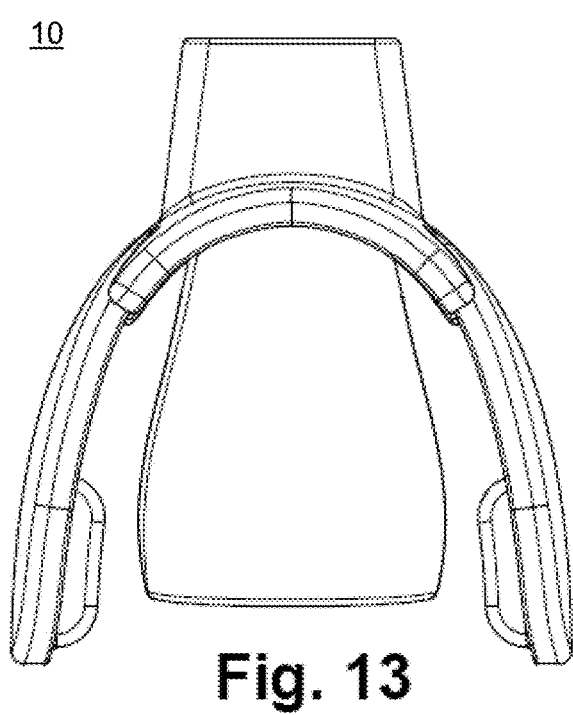
FIG. 13 is a top view of the intraoral phototherapy device of FIG. 8.
Figure 14:
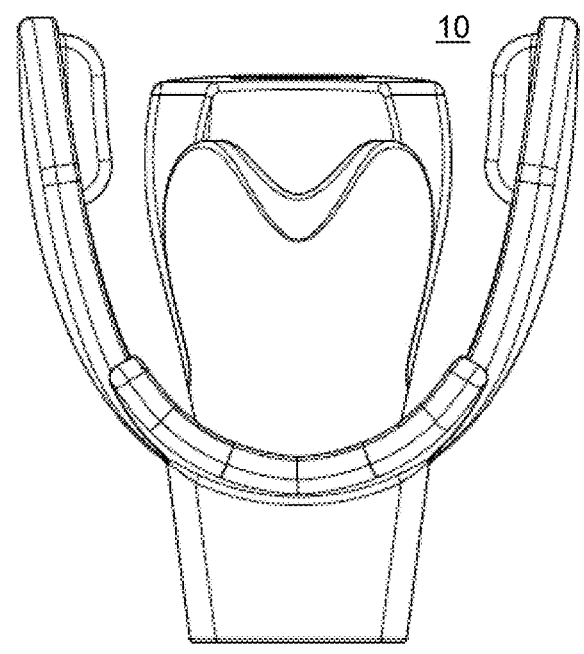
FIG. 14 is a bottom view of the intraoral phototherapy device of FIG. 8.
Figure 15:
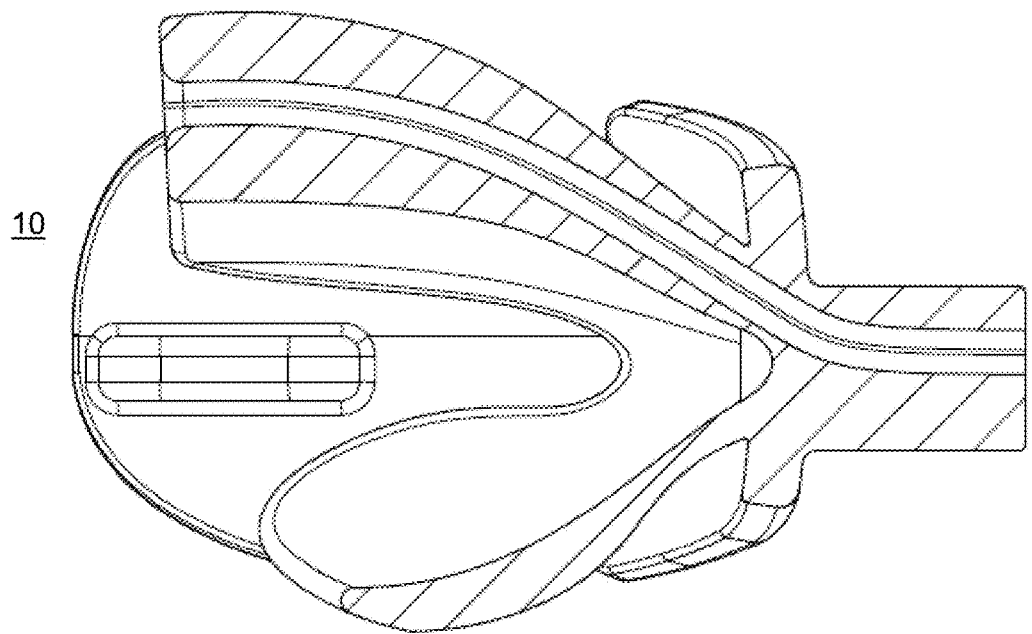
FIG. 15 is a side cut away view of the intraoral phototherapy device of FIG. 12.

The present invention is described below in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

DETAILED DESCRIPTION

According to an exemplary embodiment, an intraoral phototherapy device is provided that improves tissue illumination. Oral tissue illumination is particularly difficult in the oral cavity inside of the teeth. That is, it is particularly difficult to illuminate the roof of the mouth, floor of the mouth, sides of the tongue, and/or ventral surface of the tongue. The intraoral phototherapy device improves illumination of these tissues using a bifurcated central projection that receives a portion of the tongue.

According to another exemplary embodiment, an intraoral phototherapy device is provided that includes a breathing tube. While receiving phototherapy, it is often difficult to illuminate the back of the mouth due to obstructions caused by other tissues (e.g., the tongue). By including a breathing tube, the phototherapy device improves illumination of the back of the throat by allowing the patient to vocalize certain sounds (such as "ooooo" or "ahhhhh") while receiving phototherapy.

According to a further exemplary embodiment, an intraoral phototherapy device is provided that enables individualized phototherapy based on patient need. The intraoral phototherapy device allows for separate control of light emission from areas of the intraoral phototherapy device, such that different tissues receive different optical doses.

In the embodiment depicted in FIGS. 1-7, an intraoral phototherapy device 10 is shown for illuminating targeted regions of an oral cavity of a patient. The intraoral phototherapy device 10 includes a main body portion 12 shaped (1) to conform to contours of the oral cavity when inserted therein and (2) to direct light to the targeted regions of the oral cavity. The main body portion includes a pair of laterally spaced side wings 14 and a bifurcated central projection 16. The side wings 14 are sized and shaped to be received between teeth and cheeks of the patient on opposite sides of the oral cavity. The pair of laterally spaced side wings 14 includes an inner surface 20 facing towards a tongue and an outer surface 22 opposite the inner surface 20 and facing towards the cheeks when inserted into the oral cavity. The bifurcated central projection 16 has a first projection 30, and a second projection 32 separated from the first projection 30. The first projection 30 and the second projection 32 are sized and shaped to receive a portion of a tongue of the patient between the first projection 30 and the second projection 32.

The received portion of the tongue (i.e., the portion of the tongue received between the first projection 30 and the second projection 32) may be at least 25% of an oral tongue of the patient. Use of the term "oral tongue" herein refers to a body of the tongue between the apex of the tongue and the foramen cecum of the tongue. In another embodiment, the received portion of the tongue includes at least 15%, at least 50% or at least 75% of the oral tongue. In a further embodiment, the received portion of the tongue includes at least one of (1) a portion of the frenulum or (1) at least one of the submandibular salivary ducts.

In the embodiment depicted in FIGS. 1-15, the first projection 30 is an upper projection and the second projection 32 is a lower projection. The upper projection 30 has an outer surface 34 facing towards a roof of the oral cavity and an inner surface 36 facing towards a top of the tongue when inserted into the oral cavity. The lower projection 32 has an inner surface 38 facing towards a bottom of the tongue and an outer surface 40 facing towards a floor of the oral cavity when inserted into the oral cavity.

In one embodiment, the intraoral phototherapy device 10 includes light emitters 50 positioned on the main body portion 12. The light emitters 50 are configured to emit the light that is directed onto the targeted regions of the oral cavity. The light emitters 50 may be segmented into groups based on the tissues or regions of the oral cavity that the light emitters 50 illuminate when the intraoral phototherapy device 10 is inserted into the oral cavity. As is described in further detail below, the groups of light emitters 50 may be separately controlled to vary the optical dose received by different tissues of the oral cavity during phototherapy. The light emitters 50 may include at least one of buccal light emitters 52, top tongue light emitters 54, bottom tongue light emitters 56, mouth roof light emitters 58, or mouth floor light emitters 60. The groups of light emitters 50 may be separated in name only. That is, the different groups of light emitters 50 may be controlled together with other light emitter groups. Similarly, different light emitter groups may be independently controlled.

The buccal light emitters 52 are positioned on the outer surface 22 of the side wings 14 and illuminate the buccal tissues. The top tongue light emitters 54 are positioned on the inner surface 36 of the upper projection 30 and illuminate a top surface (also referred to as dorsal surface) of the tongue. The bottom tongue light emitters 56 are positioned on the inner surface of the lower projection 32 and illuminate a bottom surface (also referred to as a ventral surface) of the tongue. The mouth roof light emitters 58 are positioned on the outer surface 34 of the upper projection 30 and illuminate a roof of the oral cavity. The mouth floor light emitters 60 are positioned on the outer surface 40 of the lower projection 32 and illuminate a floor of the oral cavity (underneath the tongue). Different embodiments of the intraoral phototherapy device 10 may include different groups of light emitters 50.

In one embodiment, the light emitters 50 include the buccal light emitters 52, the top tongue light emitters 54, and the bottom tongue light emitters 56. This allows the light emitters 50 to illuminate the buccal tissues, the top of the tongue, and the bottom of the tongue. In another embodiment, the light emitters 50 additionally include mouth roof light emitters 58 and mouth floor light emitters 60. The inclusion of these additional light emitters 50 enable the intraoral phototherapy device 10 to also illuminate the roof of the oral cavity and the floor of the oral cavity.

The main body portion 12 may be made of a material that is at least partially transparent to light emitted by the light emitters 50. For example, the main body portion 12 may be made at least partially made from a soft, flexible, optically clear silicone material While the above described embodiments include light emitters 50 housed on the main body portion, the intraoral phototherapy device 10 may instead receive the light directed onto the targeted regions from a light source external to the main body portion 12. The light source may direct light to the main body portion 12 and the main body portion act as a light guide to may both transmit and emit the light that illuminates the targeted regions of the oral cavity. For example, the light source may be attached to the main body portion 12 via a light guide. In this example, the light source may be a light box supported by an external structure (e.g., a table). In another example, the light source may be physically mounted to a tab 61 on an external surface of the main body portion 12. In this example, the light source may be one or more light emitters 50 enclosed in a housing that includes a power source (such as a battery).

In one embodiment, the light source is a remote light source that is optically coupled to rearwardly protruding ends of the main body portion 12 via a fiber optic cable. In an embodiment, the remote light source includes one or more LEDs or a laser.

In some embodiments, one or more portions of the main body portion protrude rearwardly beyond the side wings 14 for optically coupling of a light source thereto. For example, the light source may be one or more LEDs directly optically coupled to rearwardly protruding ends (also referred to as a tab) 61 of the main body portion 12. The light source may comprise multiple light sources and the output of the light sources may vary in optical power. For example, the LEDs may be mounted on a circuit board inside a housing attached to the tab 61 with the LEDs in substantially direct contact with the tab 61.

In some embodiments, the main body portion 12 acts as a light guide for transmitting and directing light to targeted regions of the oral cavity by internal reflection and causing light to be emitted therefrom by providing disruptions or lenses along the length of the main body portion 12. For example, the main body portion 14 may be made of an optically transparent soft flexible biocompatible polymeric material such as silicone. As an example, the main body portion 12 may be made of different formulations of polycarbonate, polymethyl methacrylate, polystyrene, nylon, acrylonitrile butadiene styrene, polyolefin, or other biocompatible thermoplastic elastomer formulations.

The light emitters 50 may include a plurality of light emitting diodes (LEDs). The light emitters 50 may additionally include one or more lasers. As will be understood by one of ordinary skill in the art, the light emitters 50 may include any suitable source of electromagnetic radiation. The light emitters 50 may emit light having a wavelength from 600 nm to 1000 nm. For example, the light emitters 50 may emit electromagnetic radiation having a wavelength approximately equal to at least one of 630 nm, 660 nm, 670 nm, 810 nm, or 880 nm.

The different groups of light emitters may include any number of light emitters. The different groups of light emitters may also include light emitters having different properties. For example, the position and number of light emitters 50 in a group may be chosen depending on the target regions being treated and based on properties of the user (e.g., size, weight, skin tone, etc.).

In one embodiment, the main body portion 12 additionally includes bite pads 62 located on the inner surfaces 20 of the side wings 14. The bite pads 62 are protrusions projecting inward (i.e., towards the interior of the oral cavity) from the inner surface 20 and are positioned on the side wings 14 for engagement by teeth of the patient. The bite pads 62 are used to secure the side wings 14 in place when the main body portion 12 is inserted into the oral cavity of the patient.

The bite pads 62 may additionally be used to create a gap between the teeth for illuminating the lateral surfaces of the tongue. For example, in one embodiment the light emitters 52 include lateral tongue light emitters 64 positioned to emit light from at least one of the inner surface 20 of the side wings 14 or a distal surface 66 of the bite pads 62, such that the light emitted by the tongue light emitters 64 projects inward (1) from the inner surface 20 and/or (2) from the distal surface 66, and between the molar teeth to illuminate a lateral surface of the tongue when the main body portion 12 is inserted into the oral cavity. That is, when positioned in the oral cavity, the bite pads 62 create a gap between the teeth. By projecting light from at least one of the inner surface 20 or the distal surface 66, the light from the lateral tongue light emitters 64 passes through the gap in the teeth and illuminates the lateral tongue tissues. For example, the bite pads 62 may be positioned towards a distal end of the side wings, such that the bit pads 62 engage with the molar teeth when the intraoral phototherapy device 10 is inserted into the oral cavity.

The bite pads 62 may be made from any suitable material for transmitting light and for engaging with the teeth. For example, the bite pads may be made from the same material as the main body portion 12.

In one embodiment, the upper portion 30 additionally has a distal surface 70 located between the upper surface 34 of the upper portion 30 and the lower surface 36 of the upper portion 30. In this embodiment, the light emitters 52 include a tonsil light emitter 72 located on or emitting light from the distal surface 70 of the upper portion 30. The tonsil light emitter 72 are configured to emit light that is directed onto a tonsillar region of the oral cavity when inserted into the oral cavity. The tonsillar region may include the back of the mouth comprising at least one of the tonsils, uvula, or soft palate.

The tonsil light emitter 72 may be configured to emit more focused light from the main body portion 12 than from other groups of light emitters. For example, the tonsil light emitters 72 may have properties that cause the tonsil light emitters 72 to emit more directed light than light emitters of other groups.

In a particular embodiment, the inner surface 36 of the upper projection 30 has a curvature that conforms to contours of the dorsal surface of the tongue, such that light emitted from the inner surface 36 (e.g., the top tongue light emitters 54) illuminates the dorsal surface of the tongue and at least a portion of the lateral surfaces of the tongue. For example, light emitted from the inner surface 36 of the upper projection 30 may illuminate the dorsal surface of the tongue and a top portion of the lateral surfaces of the tongue.

Similarly, the inner surface 38 of the lower projection 32 may have a curvature that conforms to contours of the ventral surface of the tongue, such that light emitted from the inner surface 38 (e.g., the bottom tongue light emitters 54) illuminates the ventral surface of the tongue and at least a portion of the lateral surfaces of the tongue. For example, light emitted from the inner surface 38 of the lower projection 32 may illuminate the ventral surface of the tongue and a bottom portion of the lateral surfaces of the tongue.

Figure 16:
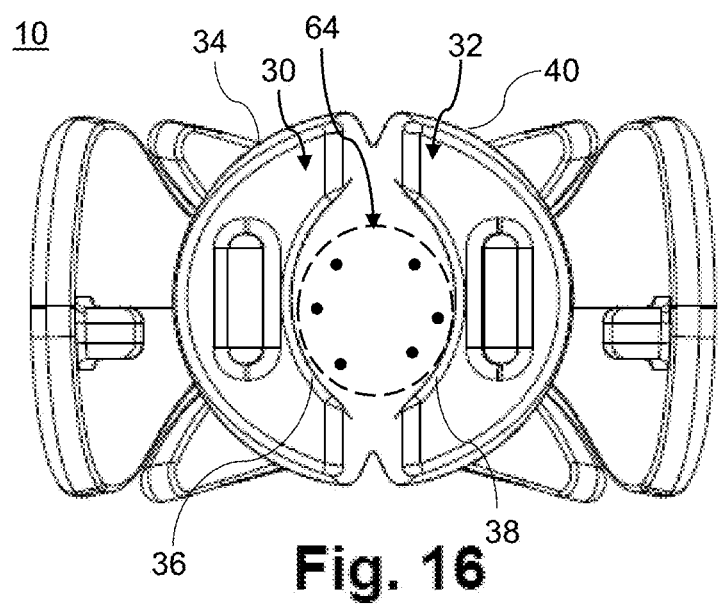
FIG. 16 is a front view of a further embodiment of the intraoral phototherapy device.
Figure 17:
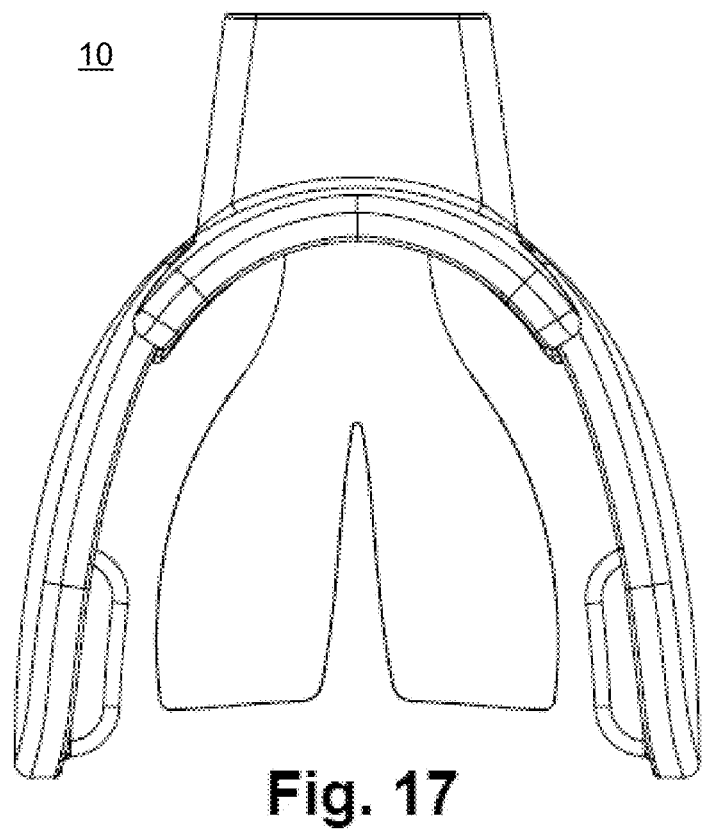
FIG. 17 is a top view of the intraoral phototherapy device of FIG. 16.

Turning to the embodiments depicted in FIGS. 16 and 17, instead of an upper projection and a lower projection, the first projection 30 may be a left projection and the second projection 32 may be a right projection. The first projection 30 has an outer surface 34 facing towards gums of the oral cavity and an inner surface 36 facing towards a first lateral surface (i.e., one side) of the tongue. The second projection 32 has an outer surface 40 facing towards the gums of the oral cavity and an inner surface 38 facing towards a second lateral surface (i.e., another side) of the tongue.

Similar to the embodiment described above and depicted in FIGS. 1-15, the intraoral phototherapy device 10 may also include light emitters 50 positioned on the main body portion 12 when including a left and right projection 30, 32. The light emitters 52 may include at least one of buccal light emitters 52, lateral tongue light emitters 64, mouth roof light emitters 58, or mouth floor light emitters 60. The buccal light emitters 52 are positioned on the outer surface 22 of the side wings 14. The lateral tongue light emitters 64 are positioned on a central portion of the inner surface 36, 38 of at least one of the left projection 30 or the right projection 32. The mouth roof light emitters 58 are positioned on the outer surface 34, 40 of at least one of the left projection 30 or the right projection 32. The mouth floor light emitters 60 may be positioned on the outer surface 34, 40 of at least one of the left projection 30 or the right projection 32.

For example, the mouth roof light emitters 58 may be positioned on at most a top half, a top third, or a top quarter of the outer surface 34, 40 of the left projection 30 and/or the right projection 32. Similarly, the mouth floor light emitter 60 may be positioned on at most a bottom half, a bottom third, or a bottom quarter of the outer surface 34, 40 of the left projection 30 and/or the right projection 32. In this way, both the mouth roof light emitters 58 and the mouth floor light emitters 60 may be housed on one or more of the left projection 30 or the right projection 32.

In one embodiment, the light emitters 50 include the buccal light emitters 52, the lateral tongue light emitters 64, the mouth roof light emitters 58, and the mouth floor light emitters 60. At least one of the left portion 30 or the right portion 32 may additionally have a distal surface 70 located between the inner surface 36 and the outer surface 34. In such an embodiment, the light emitters 50 include the tonsil light emitter 72 located on the distal surface 70.

As described above, the targeted regions of the oral cavity may include at least one of the tongue, mandibular and maxillary buccal surfaces of the oral cavity, the floor and roof of the oral cavity, and tonsillar tissues. In one embodiment, the targeted regions of the oral cavity include the tongue, mandibular and maxillary buccal surfaces of the oral cavity, the floor and roof of the oral cavity, and tonsillar tissues. As described in further detail below, the intraoral phototherapy device 10 may apply phototherapy unevenly across the tissues by varying the optical dose received by different tissues. This variation in optical dose may be due to present medical issues in these tissues (e.g., lesions, sores, etc.). Alternatively, this variation may be due to a statistically higher likelihood of these tissues experiencing such issues. In this example, phototherapy may be used as a preventative treatment.

That is, the particular dose of optical power delivered to the target regions may vary between at least two of the target regions. For example, the target regions may include at least one of: a tonsillar region, buccal tissues of an oral cavity, a hard palate, a soft palate, or the tongue. The particular dose of optical power delivered to the different tissues may be varied based on known effective optical doses for treating different issues. For example, the particular dose for the tonsillar region may be different from the particular dose of optical power delivered to the hard palate.

The particular dose of optical power for each of the target regions may be between 10 milliwatts/cm$^2$ and 150 milliwatts/cm$^2$. The particular dose of optical power received by each of the target regions may not vary between the target regions by more than 20%.

The intraoral phototherapy device may be used in a number of applications, several examples of which include oral mucositis, acute necrotizing ulcerative gingivitis (ANUG), periodontal diseases, trismus, decreasing recovery time from oral surgery, light delivery for orthodontics, and photodynamic light therapy, e.g., to activate a chemical mouthwash.

As shown in the depicted embodiments, the main body portion 12 may include vertical wings 92. The vertical wings 92 include an upper wing 94 vertically spaced from a lower wing 96. The vertical wings 92 are sized and shaped to be received between the teeth and lips of the patient. The vertical wings 92 include an inner surface 98 facing towards the tongue and an outer surface 100 opposite the inner surface 98. The outer surface 100 faces towards the lips when inserted into the oral cavity. In this embodiment, the light emitters may include labial emitters 102 positioned on the outer surface 100 of the vertical wings 92, such that the light emitted by the labial light emitters 102 illuminates the lip mucosa when the main body 12 is positioned within the oral cavity.

In the embodiments depicted in FIGS. 8-17, the intraoral phototherapy device 10 includes at least one inner channel 80 extending between an opening 82 on an interior of the main body portion 12 and an exterior of the main body portion 12. The inner channel 80 provides an air path between the oral cavity and an environment outside of the oral cavity. The air path allows for improved patient breathing during treatment using the intraoral phototherapy device 10.

In the embodiment depicted in FIGS. 8-17, the opening 82 of the inner channel 80 on the interior of the main body portion is located on at least one of the first projection 30 or the second projection 32. In the embodiment depicted in FIGS. 18 and 19, the opening 82 of the inner channel 80 on the interior of the main body portion is located on the interior surface 20 of at least one of the side wings 14. For example, in the depicted embodiment there are two inner channels 80 having an opening 82 for one of the channels 80 located on each of the side wings 14.

The inner channel 80 may be configured to act as a breathing tube when the intraoral phototherapy device 10 is placed in the oral cavity. In embodiments including the inner channel 80, a patient is able to exhale, opening the back of the throat to expose the soft tissues for phototherapy. For example, a patient may be asked to say "00000" during exhalation to more fully open the back of the throat during treatment. The inner channel 80 may be formed from a same or different material as the main body portion 12.

In one embodiment, at least one of the first projection 30 or the second projection 32 include a surface irregularity 86 on an inner surface 36, 38. The surface irregularity 86 is configured to aid in placement of the tongue between the inner surfaces 36, 38 of the first projection 30 and the second projection 32 by allowing a patient to feel the surface irregularity 86 while positioning their tongue in between the central projection 16. The surface irregularity 86 may be positioned on the first projection 30 and/or the second projection 32 such that the surface irregularity 86 is only detectable by the tongue (i.e., can only be felt by the patient using their tongue) when the tongue is inserted between the inner surfaces 36, 38 of the first projection 30 and the second projection 32. For example, the surface irregularity 86 may be at least one of a surface texturing, depression, protrusion, or surface contouring. The surface irregularity 86 may be any suitable structure that is detectable by a user using touch. The surface irregularity 86 may also be positioned such that it is only detectable when the patient's tongue is inserted in the central projection 16, such that a length or sufficient portion of the tongue is illuminated by the light emitted from the main body portion 12.

In another embodiment, the intraoral phototherapy device 10 includes at least one sensor for detecting tongue placement. If the tongue is not detected by the sensor, then the intraoral phototherapy device 10 may issue a notification (e.g., a sound, vibration, or light) indicating that the tongue is improperly placed.

Figure 18:
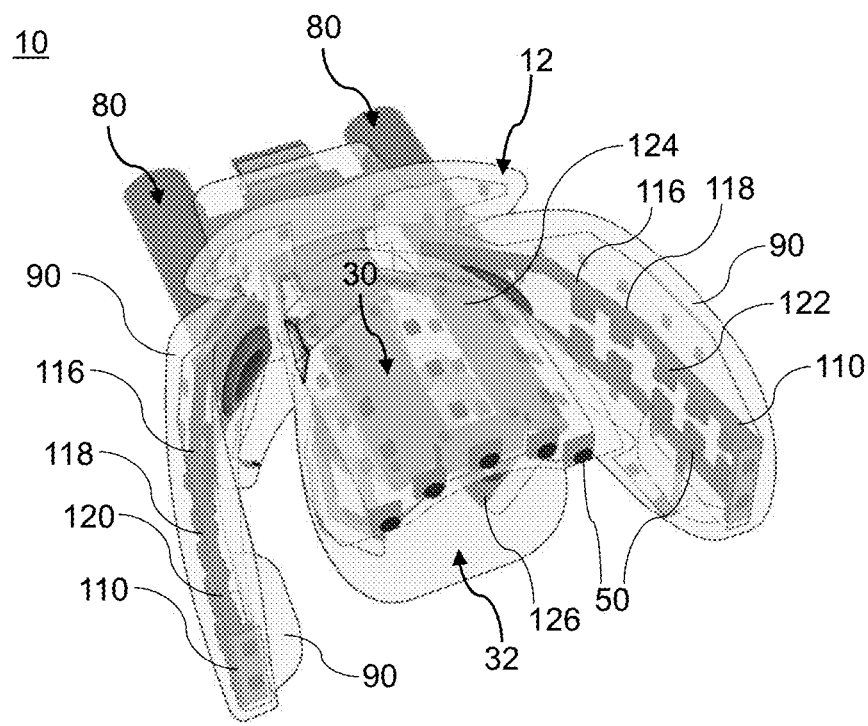
FIG. 18 is a top perspective view of another embodiment of the intraoral phototherapy device.
Figure 19:
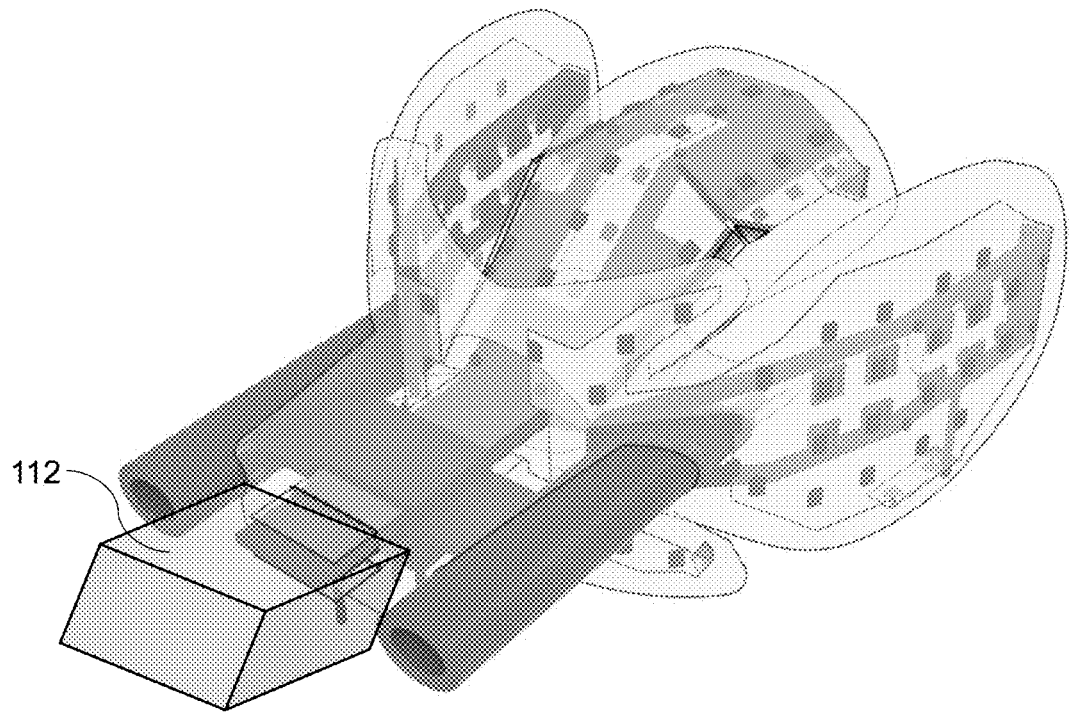
FIG. 19 is a rear perspective view of the intraoral phototherapy device of FIG. 18.
Figure 20:
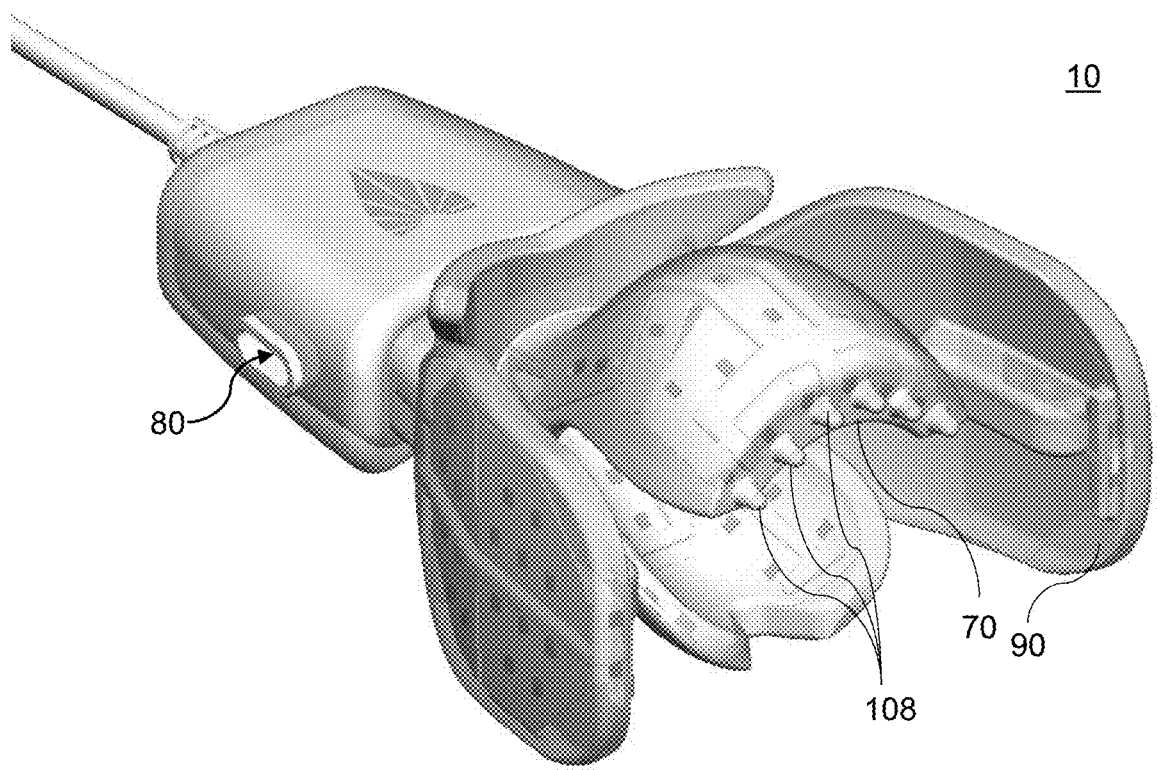
FIG. 20 is a top perspective partially transparent view of a further embodiment of the intraoral phototherapy device including lenses.
Figure 21:
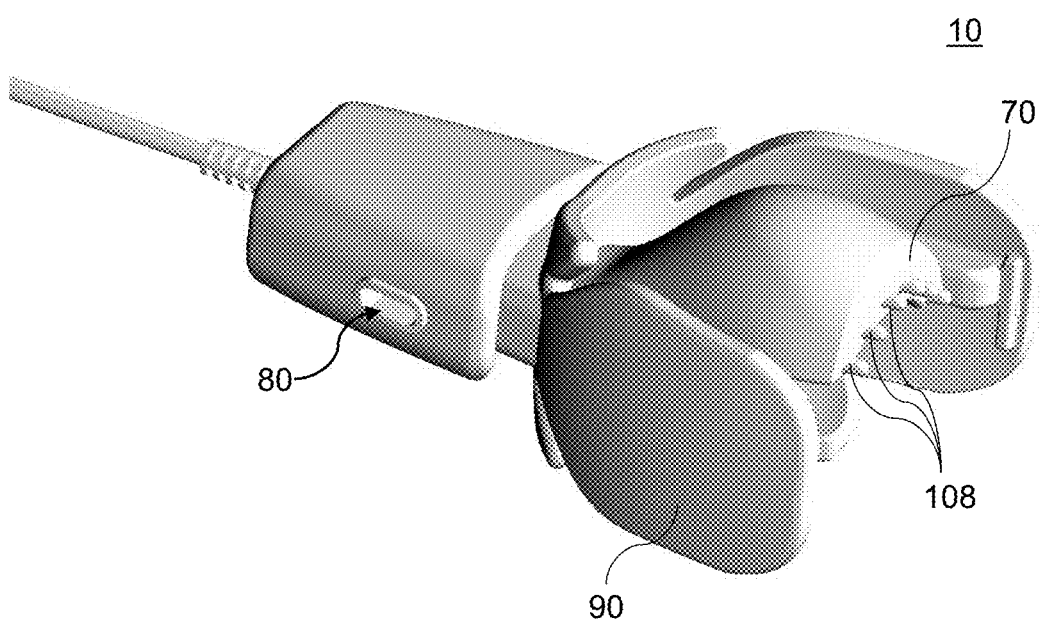
FIG. 21 is a top perspective view of the intraoral phototherapy device of FIG. 20.

In the embodiment depicted in FIGS. 18 and 19, the main body portion 12 includes a coating 90 covering the light emitters 50. The coating 90 may include lenses positioned to alter a distribution of light exiting from the coating 90. For example, the coating 90 may increase a diffusion of light exiting the coating 90 to improve a uniformity of tissue illumination by the light emitters 50. Alternatively or additionally, the coating 90 may increase the directionality of light exiting some areas of the coating to preferentially illuminate particular locations (e.g., associated with particular tissues) when the main body portion 12 placed in the oral cavity. In an embodiment, the coating 90 includes disruptions or lens patterns to cause light to be emitted from the intraoral phototherapy device 10 in a controlled manner. For example, in the embodiment shown in FIGS. 20-23, the intraoral phototherapy device 10 includes lenses 108 that alter the distribution of light exiting the distal surface 70.

Figure 22:
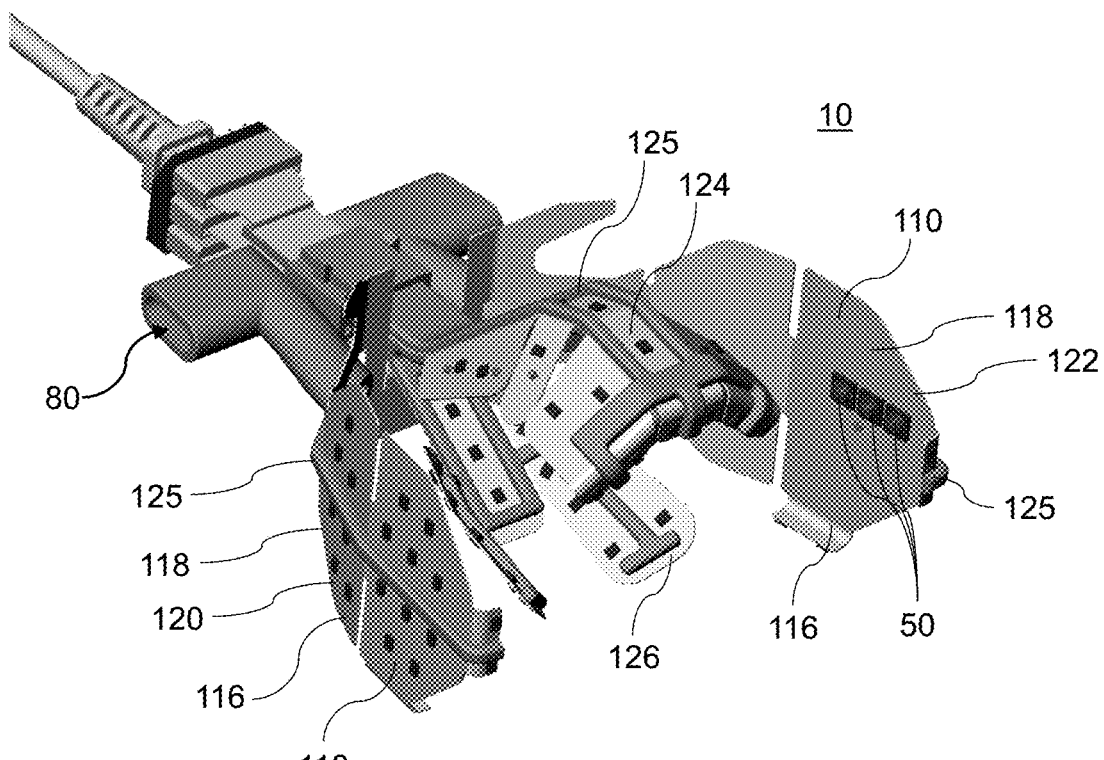
FIG. 22 is a top perspective view showing the substrate of the intraoral phototherapy device of FIG. 20.
Figure 23:
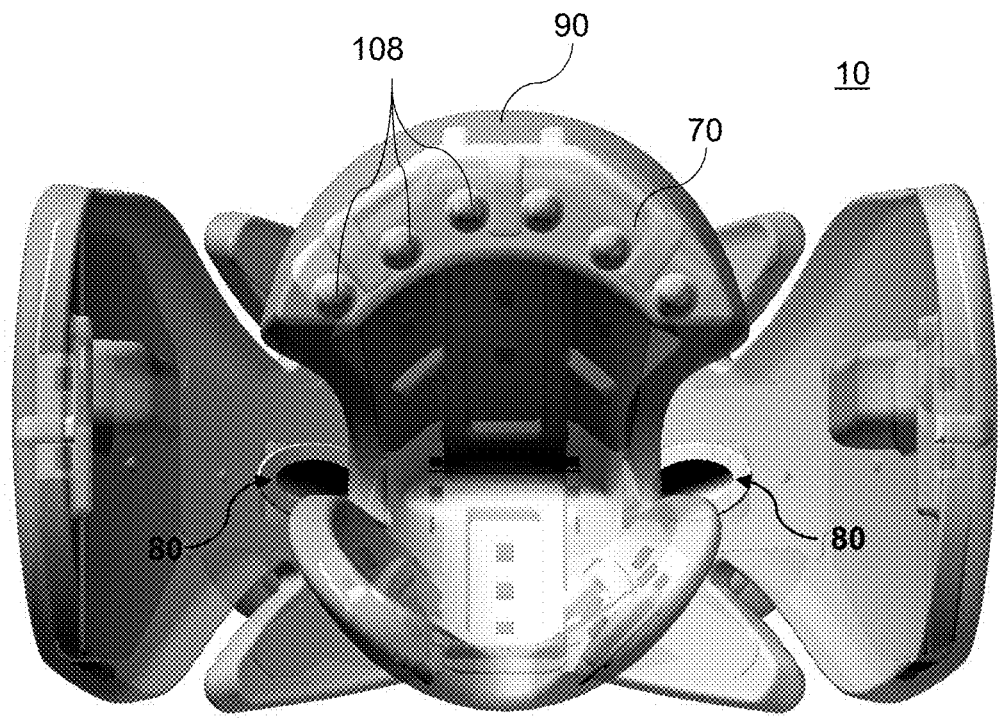
FIG. 23 is a front perspective partially transparent view of the intraoral phototherapy device of FIG. 20.
Figure 24:
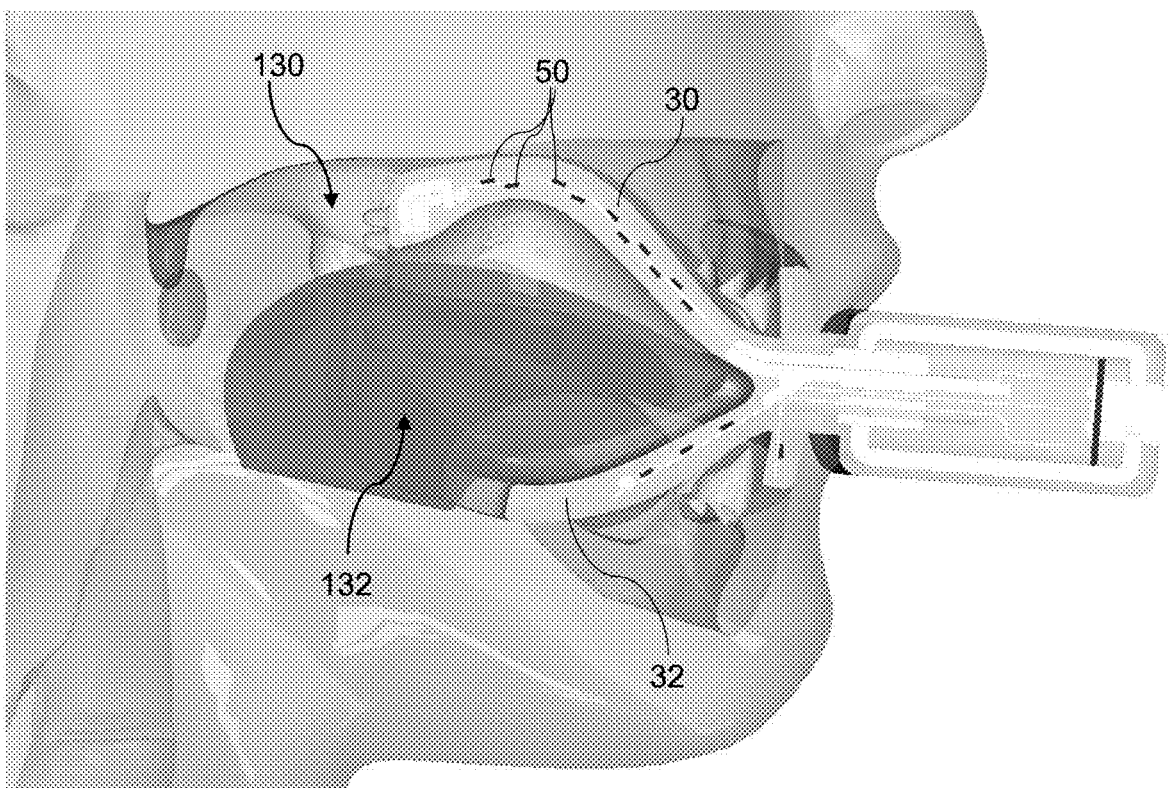
FIG. 24 is a side cut away view of an embodiment of the intraoral phototherapy device located in the oral cavity.
Figure 25:
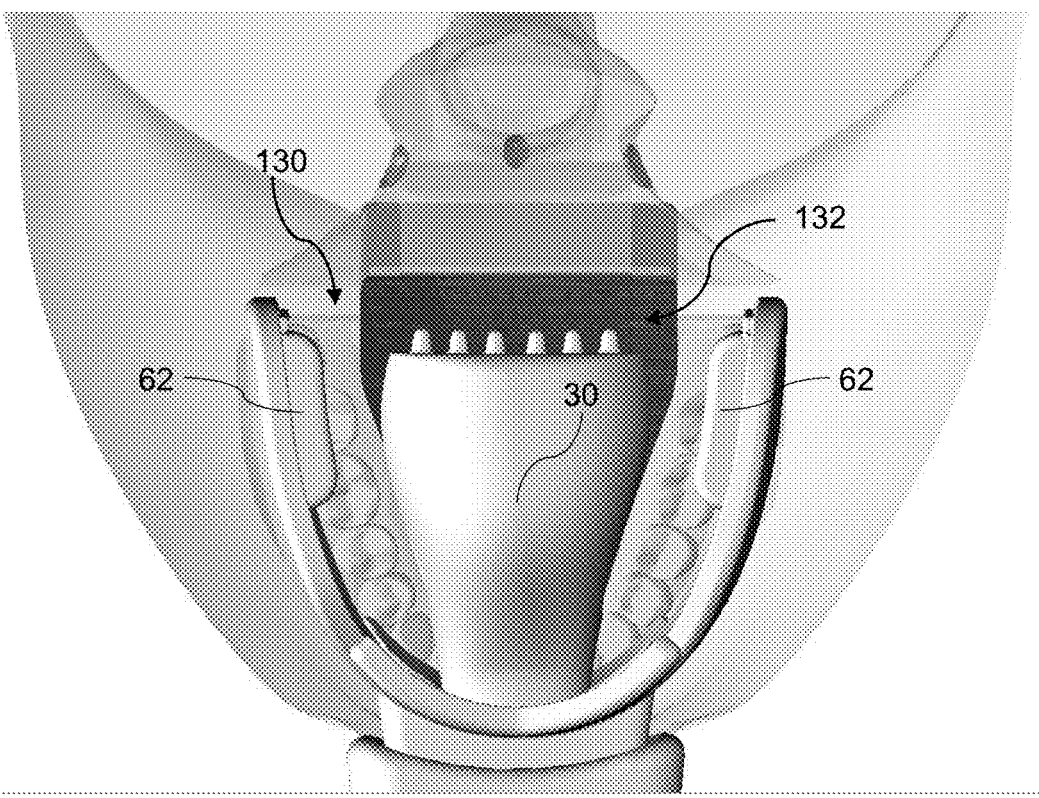
FIG. 25 is a top cut away view of the intraoral phototherapy device of FIG. 24 located in the oral cavity.
Figure 26:
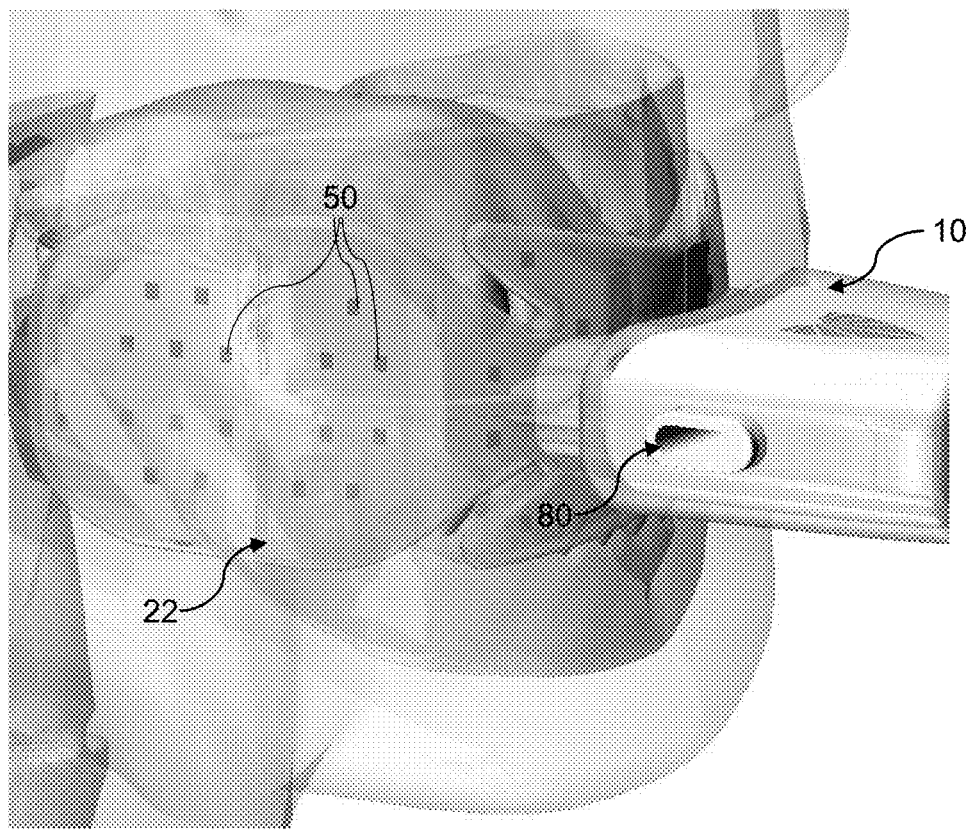
FIG. 26 is a front perspective partially transparent view of an embodiment of the intraoral phototherapy device located in the oral cavity.
Figure 27:
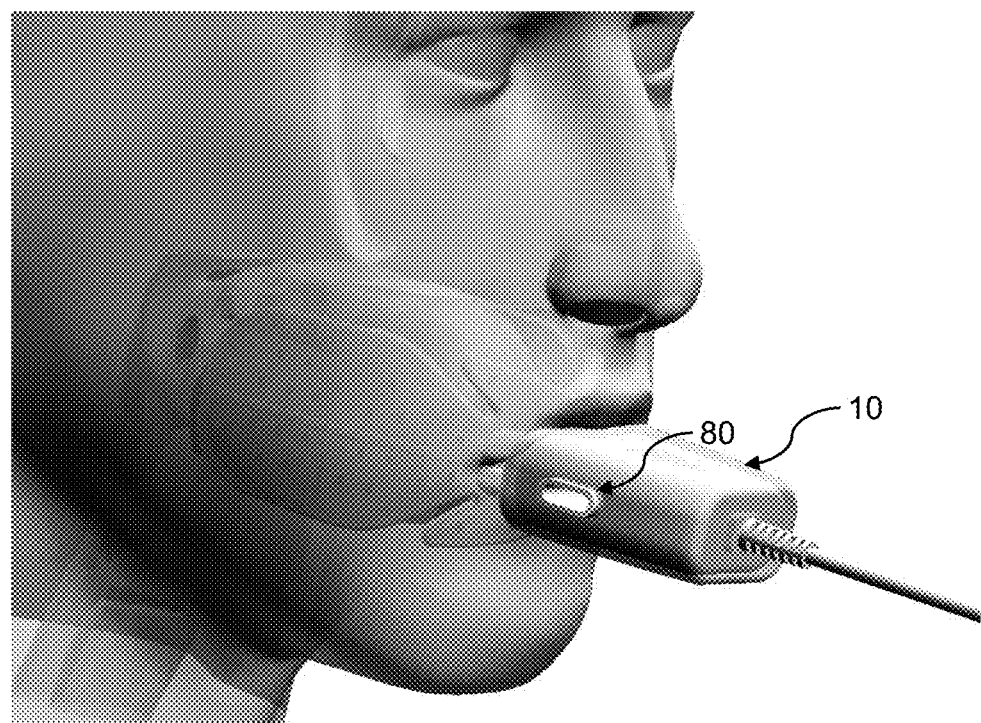
FIG. 27 is a front perspective less transparent view of the embodiment of the intraoral phototherapy device of FIG. 25 located in the oral cavity.

In the embodiment shown in FIGS. 20-23, the main body portion 12 includes a substrate 110 and the coating 90. The light emitters 50 are mounted to the substrate 110 and also receive electrical power from the substrate 110. The coating 90 at least partially covers the substrate 110 and the light emitters 50. As shown in FIG. 22, the intraoral phototherapy device 10 may additionally include circuitry 112 and the substrate 110 may include a plurality of separate circuit boards 116 including a pair of side wing circuit boards 118 (i.e., a first side wing circuit board 120 and a second side wing circuit board 122), a first central projection circuit board 124, and a second central projection circuit board 126. The substrate 90 may include a support structure 125 that supports the circuit boards 116. The circuit boards 116 may be printed circuit boards (PCBs) such as flexible PCBs. The support structure 125 may support the circuit boards 116 before the coating 90 is applied. The coating 90 may be overmolded onto the circuit boards 116 being supported by the support structure. Each of the separate circuit boards 116: interfaces with the circuitry 112, receives electrical power from the circuitry 112, and supplies the electrical power to the light emitters 50. For example, the light emitters 50 may be attached to the circuit boards 116 and the circuit boards 116 may be formed to control the direction of light travel from the intraoral phototherapy device 10.

In one embodiment, the circuitry 112 is configured to separately and independently supply electrical power to at least two of the circuit boards 116, such that the electrical power received by the at least two circuit boards 116 is separately controlled by the circuitry 112. For example, the circuitry 112 may receive a control signal from an electronic device specifying optical power to be supplied by at least one of the circuit boards 116. The circuitry 112 may control the electrical power supplied to the circuit boards 116 based on the received control signal. As an example, if a patient has lesions on the roof of their mouth but no lesions on their cheeks, then an external device may be used to communicate to the circuitry 112 (via the control signal) that a higher dose of optical power is needed on the roof of the mouth compared to the cheeks (i.e., buccal tissues). In this example, the circuitry 112 may supply electrical power to the first central projection circuit board 124, such that the mouth roof light emitters 58 supply a larger optical dose compared to the light emitters 50 of the side wing circuit boards 118.

The circuitry 112 may vary the optical dose delivered by the different groups of light emitters 50 by varying the sum of electrical power supplied to the groups of light emitters 50. For example, when supplying electrical power, the circuitry 112 may supply the same level of electrical power to the circuit boards 116, but the circuitry 112 may vary the amount of time that electrical power is supplied to the various boards 116. As an example, the circuitry 112 may use pulse width modulation (PWM) to control the total amount of time supplied to the different circuit boards 116.

The circuitry 112 may have various implementations. For example, the circuitry 112 may include any suitable device, such as a processor (e.g., CPU), programmable circuit, integrated circuit, memory and I/O circuits, an application specific integrated circuit, microcontroller, complex programmable logic device, other programmable circuits, or the like. The circuitry 112 may also include a non-transitory computer readable medium, such as random-access memory (RAM), a read-only memory (ROM), an erasable programmable read-only memory (EPROM or Flash memory), or any other suitable medium. Instructions for performing the method described below may be stored in the non-transitory computer readable medium and executed by the circuitry 112. The circuitry 112 may be communicatively coupled to the computer readable medium and a network interface through a system bus, mother board, or using any other suitable structure known in the art. The circuitry 112 may receive parameters for controlling the illumination source 14 via the network interface. Alternatively or additionally, the circuitry 112 may receive particular optical doses for different tissues from the network interface and the circuitry 112 may control the illumination source 14 so that the received optical doses are received by the respective tissues.

FIGS. 24-27 show an embodiment of the intraoral phototherapy device 10 positioned within the oral cavity 130. As described above, received portion of the tongue may be at least 25% of an oral tongue 132 of the patient. Use of the term "oral tongue" herein refers to a body of the tongue between the apex of the tongue and the foramen cecum of the tongue. In another embodiment, the received portion of the tongue includes at least 15%, at least 50% or at least 75% of the oral tongue. In a further embodiment, the received portion of the tongue includes at least one of (1) a portion of the frenulum or (1) at least one of the submandibular salivary ducts.

Figure 28:
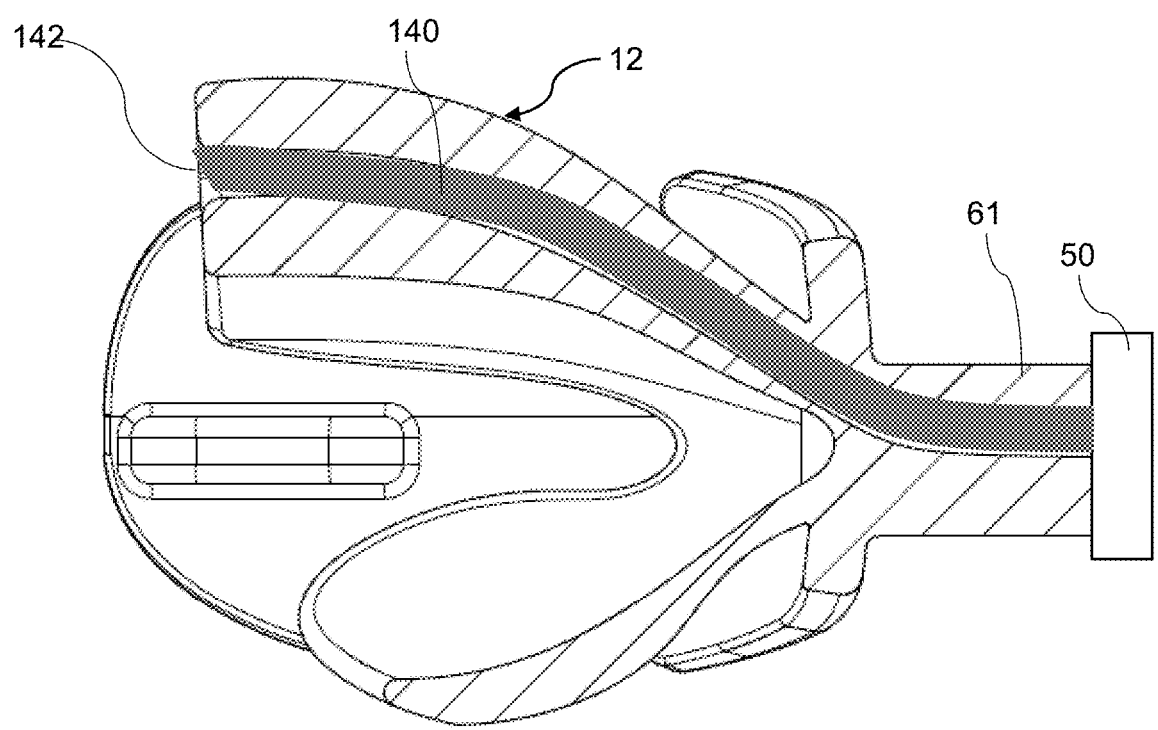
FIG. 28 is a side cut away view of an intraoral phototherapy device including a light guide.

As described above, the intraoral phototherapy device 10 may receive the light directed onto the targeted regions from a light source external to the main body portion 12. In the embodiment shown in FIG. 28, the light emitters 50 are physically mounted to a tab 61 on an external surface of the main body portion 12. The light emitted by the light emitters 50 is received by a light guide 140 that directs the light from the light emitters 50 to an emission surface 142 of the main body portion 12. For example, the light guide 140 may be a portion of the main body portion 12 that acts as a light guide to both transmit and emit the light that illuminates the targeted regions of the oral cavity. While the depicted embodiment shows only a single light guide, multiple light guides may be used to project light onto the target tissues.

The light guide(s) 140 may be over molded in Silicone with the flexible circuit boards described above. The light guide(s) 140 geometry may also be incorporated with the support structure 125 that holds onto the circuit boards 116.

In any of the embodiments, a reflective coating 24 may be provided on the inwardly facing sides of the side wings to reflect light out through the outwardly facing sides of the side wings.

In any of the embodiments, the side wings may have a curvature that is contoured to mandibular and maxillary buccal surfaces of the oral cavity for emitting light thereto.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. An intraoral phototherapy device for illuminating targeted regions of an oral cavity of a patient, the device comprising:
    a main body portion shaped to conform to contours of the oral cavity when inserted therein to direct light to the targeted regions of the oral cavity, wherein the main body portion includes:
        a pair of laterally spaced side wings sized and shaped to be received between teeth and cheeks of the patient on opposite sides of the oral cavity, the pair of laterally spaced side wings including an inner surface facing towards a tongue and an outer surface opposite the inner surface and facing towards the cheeks when inserted into the oral cavity; and
        a bifurcated central projection having a first projection and a second projection separated from the first projection, wherein:
            the first projection and the second projection are sized and shaped to receive a portion of a tongue of the patient between the first projection and the second projection;
            the received portion of the tongue is at least 25% of an oral tongue of the patient;
            the first projection is an upper projection having an outer surface facing towards a roof of the oral cavity and an inner surface facing towards a top of the tongue when inserted into the oral cavity; and
            the second projection is a lower projection having an inner surface facing towards a bottom of the tongue and an outer surface facing towards a floor of the oral cavity when inserted into the oral cavity;
    wherein the main body portion additionally includes bite pads located on the inner surfaces of the side wings comprising protrusions projecting inward from the inner surface and positioned on the side wings for engagement between upper teeth and lower teeth of the patient to:
        secure the side wings in place when the main body portion is inserted into the oral cavity of the patient; and
        form a gap between the upper and lower teeth; and
    wherein the light emitters include lateral tongue light emitters positioned to emit light from at least one inner surface of the side wings or a distal surface of the bite pads, such that the light emitted by the tongue light emitters projects inward from the inner surface of the side wings or the distal surface of the size wings and passes between the teeth through the gap to illuminate a lateral surface of the tongue when the main body portion is inserter into the oral cavity.

2. The device of claim 1, further comprising light emitters positioned on the main body portion and configured to emit the light that is directed onto the targeted regions of the oral cavity, wherein:
    the light emitters include at least one of buccal light emitters, top tongue light emitters, bottom tongue light emitters, mouth roof light emitters, or mouth floor light emitters; and
    the buccal light emitters are positioned on the outer surface of the side wings, the top tongue light emitters are positioned on the inner surface of the upper projection, the bottom tongue light emitters are positioned on the inner surface of the lower projection, the mouth roof light emitters are positioned on the outer surface of the upper projection, and the mouth floor light emitters are positioned on the outer surface of the lower projection.

3. The device of claim 2, wherein the light emitters include the buccal light emitters, the top tongue light emitters, and the bottom tongue light emitters.

4. The device of claim 3, wherein the light emitters further include mouth roof light emitters and mouth floor light emitters.

5. The device of claim 1, wherein:
    the upper portion additionally has a distal surface located between the upper surface of the upper portion and the lower surface of the upper portion; and
    the light emitters include a tonsil light emitter located on the distal surface that is configured to emit light that is directed onto a tonsillar region of the oral cavity when inserted into the oral cavity.

6. The device of claim 1, wherein:
    the first projection is a left projection having an outer surface facing towards gums of the oral cavity and an inner surface facing towards a first lateral surface of the tongue; and
    the second projection is a right projection having an outer surface facing towards the gums of the oral cavity and an inner surface facing towards a second lateral surface of the tongue.

7. The device of claim 6, further comprising light emitters positioned on the main body portion and configured to emit the light that is directed onto the targeted regions of the oral cavity, wherein:

the light emitters include at least one of buccal light emitters, lateral tongue light emitters, mouth roof light emitters, or mouth floor light emitters; and the buccal light emitters are positioned on the outer surface of the side wings, the lateral tongue light emitters are positioned on a central portion of the inner surface of at least one of the left projection or the right projection, the mouth roof light emitters are positioned on the outer surface of at least one of the left projection or the right projection, and the mouth floor light emitters are positioned on the inner surface of at least one of the left projection or the right projection.

8. The device of claim 7, wherein the light emitters include the buccal light emitters, the lateral tongue light emitters, the mouth roof light emitters, and the mouth floor light emitters.

9. The device of claim 6, wherein:

at least one of the left portion or the right portion additionally has a distal surface located between the inner surface and the outer surface; and the light emitters includes a tonsil light emitter located on the distal surface that is configured to emit light that is directed onto a tonsillar region of the oral cavity when inserted into the oral cavity.

10. The device of claim 1, wherein the light directed onto the targeted regions of the oral cavity is generated by a light source external to the main body portion and the light is both transmitted by the main body portion and emitted from the main body portion, such that the light illuminates the targeted regions of the oral cavity.

11. The device of claim 1, wherein the targeted regions of the oral cavity include at least one of the tongue, mandibular and maxillary buccal surfaces of the oral cavity, the floor and roof of the oral cavity, and tonsillar tissues.

12. The device of claim 1, wherein the targeted regions of the oral cavity include the tongue, mandibular and maxillary buccal surfaces of the oral cavity, the floor and roof of the oral cavity, and tonsillar tissues.

13. The device of claim 1, wherein:

the main body portion additionally includes an inner channel extending between an interior opening on an interior surface of the main body portion and an exterior opening on an exterior surface of the main body portion, such that the inner channel provides an air path between the oral cavity and an environment outside of the oral cavity; and the interior opening is located on the inner surface of the pair of laterally spaced side wings.

14. The device of claim 1, wherein the main body portion includes a coating covering the light emitters and the coating includes lenses positioned to alter a distribution of light exiting from the coating.

15. The device of claim 1, wherein the main body portion is made of a material that is at least partially transparent to light emitted by the light emitters.

16. The device of claim 1, wherein:

the main body portion further including vertical wings;

the vertical wings including an upper wing vertically spaced from a lower wing;

the vertical wings are sized and shaped to be received between the teeth and lips of the patient;

the vertical wings including an inner surface facing towards the tongue and an outer surface opposite the inner surface facing towards the lips when inserted into the oral cavity; and the light emitters include labial emitters positioned on the outer surface of the vertical wings, such that the light emitted by the labial light emitters illuminates the lip mucosa when the main body is positioned within the oral cavity.

17. The device of claim 1, wherein:

the main body portion includes a substrate and a coating;

the light emitters are mounted to the substrate and receive electrical power from the substrate; and the coating covers the substrate and the light emitters.

18. The device of claim 17, further comprising circuitry, wherein:

the substrate includes a plurality of separate circuit boards including a pair of side wing circuit boards comprising a first side wing circuit board and a second side wing circuit board, a first central projection circuit board, and a second central projection circuit board;

each of the separate circuit boards interfaces with the circuitry, receives electrical power from the circuitry, and supplies the electrical power to the light emitters; and the circuitry is configured to separately and independently supply electrical power to at least two of the circuit boards, such that the electrical power received by the at least two circuit boards is separately controlled by the circuitry.

19. The device of claim 18, wherein:

the circuitry receives a control signal from an electronic device specifying optical power to be supplied by at least one of the circuit boards; and the circuitry controls the electrical power supplied to the circuit boards based on the received control signal.

20. An intraoral phototherapy device for illuminating targeted regions of an oral cavity of a patient, the device comprising:

a main body portion shaped to conform to contours of the oral cavity when inserted therein to direct light to the targeted regions of the oral cavity, wherein the main body portion includes:

a pair of laterally spaced side wings sized and shaped to be received between teeth and cheeks of the patient on opposite sides of the oral cavity, the pair of laterally spaced side wings including an inner surface facing towards a tongue and an outer surface opposite the inner surface and facing towards the cheeks when inserted into the oral cavity; and a bifurcated central projection having a first projection and a second projection separated from the first projection, wherein:

the first projection and the second projection are sized and shaped to receive a portion of a tongue of the patient between the first projection and the second projection; and the first projection and the second projection both include an inner surface;

at least one of the first projection or the second projection include on the inner surface a surface irregularity; and the surface irregularity is configured to aid in placement of the tongue between the inner surfaces of the first projection and the second projection by being positioned such that the surface irregularity interacts with the tongue when the tongue is inserted between the inner surfaces of the first projection and the second projection.

21. The device of claim 20, wherein:

the first projection is an upper projection having an outer surface facing towards a roof of the oral cavity and an inner surface facing towards a top of the tongue when inserted into the oral cavity; and the second projection is a lower projection having an inner surface facing towards a bottom of the tongue and an outer surface facing towards a floor of the oral cavity when inserted into the oral cavity.

22. The device of claim 21, wherein:

the main body portion additionally includes bite pads located on the inner surfaces of the side wings comprising protrusions projecting inward from the inner surface and positioned on the side wings for engagement between upper teeth and lower teeth of the patient to:
  secure the side wings in place when the main body portion is inserted into the oral cavity of the patient; and
  form a gap between the upper and lower teeth; and the light emitters include lateral tongue light emitters positioned to emit light from at least one of the inner surface of the side wings or a distal surface of the bite pads, such that the light emitted by the tongue light emitters projects inward from the inner surface of the side wings or the distal surface of the side kings and passes between the teeth through the gap to illuminate a lateral surface of the tongue when the main body portion is inserted into the oral cavity.

23. An intraoral phototherapy device for illuminating targeted regions of an oral cavity of a patient, the device comprising:

a main body portion shaped to conform to contours of the oral cavity when inserted therein to direct light to the targeted regions of the oral cavity, wherein the main body portion includes:
  a pair of laterally spaced side wings sized and shaped to be received between teeth and cheeks of the patient on opposite sides of the oral cavity, the pair of laterally spaced side wings including an inner surface facing towards a tongue and an outer surface opposite the inner surface and facing towards the cheeks when inserted into the oral cavity; and
  a bifurcated central projection having a first projection and a second projection separated from the first projection, wherein:
    the first projection and the second projection are sized and shaped to receive a portion of a tongue of the patient between the first projection and the second projection;
    the main body portion additionally includes at least one inner channel;
    each of the at least one inner channel extends between an interior opening on an interior surface of the main body portion and an exterior opening on an exterior surface of the main body portion, such that the inner channel provides an air path between the oral cavity and an environment outside of the oral cavity; and
    the interior opening of each of the at least inner channel is located on the inner surface of the pair of laterally spaced side wings.

24. The device of claim 23, wherein:

the first projection is an upper projection having an outer surface facing towards a roof of the oral cavity and an inner surface facing towards a top of the tongue when inserted into the oral cavity; and the second projection is a lower projection having an inner surface facing towards a bottom of the tongue and an outer surface facing towards a floor of the oral cavity when inserted into the oral cavity.

25. The device of claim 24, further comprising light emitters positioned on the main body portion and configured to emit the light that is directed onto the targeted regions of the oral cavity, wherein:

the light emitters include at least one of top tongue light emitters, bottom tongue light emitters, mouth roof light emitters, or mouth floor light emitters; and the top tongue light emitters are positioned on the inner surface of the upper projection, the bottom tongue light emitters are positioned on the inner surface of the lower projection, the mouth roof light emitters are positioned on the outer surface of the upper projection, and the mouth floor light emitters are positioned on the outer surface of the lower projection.

26. The device of claim 25, wherein the light emitters include the top tongue light emitters, and the bottom tongue light emitters.

27. The device of claim 24, wherein:

the upper portion additionally has a distal surface located between the upper surface of the upper portion and the lower surface of the upper portion; and the light emitters include a tonsil light emitter located on the distal surface that is configured to emit light that is directed onto a tonsillar region of the oral cavity when inserted into the oral cavity.

28. The device of claim 23, wherein the at least one inner channel includes a first inner channel and a second inner channel.

29. The device of claim 28, wherein the interior opening of the first inner channel and the interior opening of the second inner channel are located:

on the inner surface of the pair of laterally spaced side wings; and on opposite sides of the bifurcated central projection.

* * * * *